United States Patent  (10) Patent No.: US 12,097,074 B2
Matsumoto et al.  (45) Date of Patent: Sep. 24, 2024

(54) ULTRASONIC ELEMENT AND ENDOSCOPE

(71) Applicant: OLYMPUS CORPORATION, Tokyo (JP)

(72) Inventors: Kazuya Matsumoto, Nagano (JP); Masahiro Katashiro, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 354 days.

(21) Appl. No.: 17/672,826

(22) Filed: Feb. 16, 2022

(65) Prior Publication Data
US 2022/0167944 A1  Jun. 2, 2022

Related U.S. Application Data

(63) Continuation of application No. PCT/JP2019/033543, filed on Aug. 27, 2019.

(51) Int. Cl.
A61B 8/00 (2006.01)
A61B 8/12 (2006.01)

(52) U.S. Cl.
CPC .............. *A61B 8/4494* (2013.01); *A61B 8/12* (2013.01); *A61B 8/4444* (2013.01)

(58) Field of Classification Search
CPC ........ A61B 8/12; A61B 8/4483; B06B 1/0292
See application file for complete search history.

(56) References Cited

U.S. PATENT DOCUMENTS

| | | | |
|---|---|---|---|
| 6,854,338 B2 | 2/2005 | Khuri-Yakub et al. | |
| 7,646,133 B2 | 1/2010 | Degertekin | |
| 2006/0156821 A1 | 7/2006 | Itoh et al. | |
| 2009/0080292 A1* | 3/2009 | Wagner | B81B 3/0021 367/181 |
| 2009/0301200 A1 | 12/2009 | Tanaka et al. | |
| 2012/0123268 A1 | 5/2012 | Tanaka et al. | |
| 2015/0245811 A1* | 9/2015 | Matsumoto | A61B 8/12 600/459 |

FOREIGN PATENT DOCUMENTS

| | | |
|---|---|---|
| JP | 2006-200976 A | 8/2006 |
| JP | 2006-319712 A | 11/2006 |
| JP | 2008-510324 A | 4/2008 |
| JP | 2011035916 A * | 2/2011 |

(Continued)

OTHER PUBLICATIONS

International Search Report dated Nov. 19, 2019 issued in PCT/JP2019/033543.

*Primary Examiner* — Colin T. Sakamoto
*Assistant Examiner* — Tommy T Ly
(74) *Attorney, Agent, or Firm* — Scully, Scott, Murphy & Presser, P.C.

(57) ABSTRACT

An ultrasonic element includes at least one cMUT provided to a substrate, wherein the cMUT includes a first electrode provided to the substrate, a frame member having a cavity, a second electrode disposed to face the first electrode with the cavity interposed between the second electrode and the first electrode, and a protective layer covering the second electrode, a length of the cavity in an X axis direction being longer than a width of the cavity in a Y axis direction, the protective layer having a convex region extending in the X axis direction, a width of the convex region in the Y axis direction varying.

14 Claims, 10 Drawing Sheets

(56) References Cited

FOREIGN PATENT DOCUMENTS

| | | |
|---|---|---|
| JP | 4909279 B2 | 4/2012 |
| JP | 2013-150198 A | 8/2013 |
| JP | 5342005 B2 | 11/2013 |
| WO | 2001/033887 A1 | 5/2001 |
| WO | 2005/087391 A2 | 9/2005 |
| WO | 2007/046180 A1 | 4/2007 |

* cited by examiner

FIG. 10A  FIG. 10B  FIG. 10C
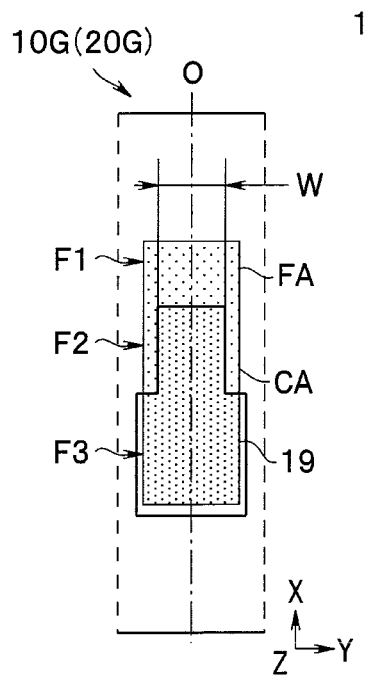
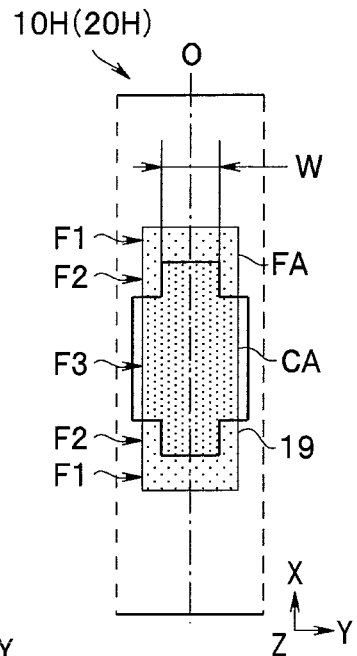
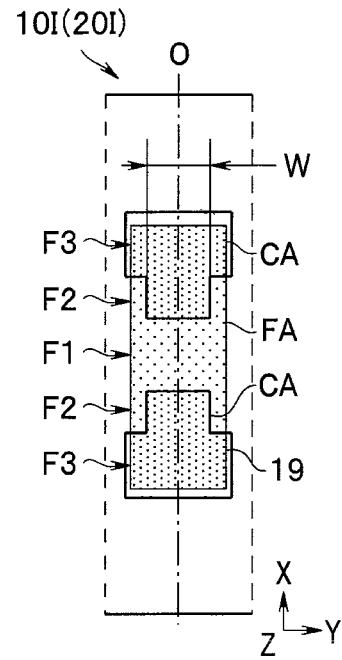
FIG. 11A  FIG. 11B  FIG. 11C
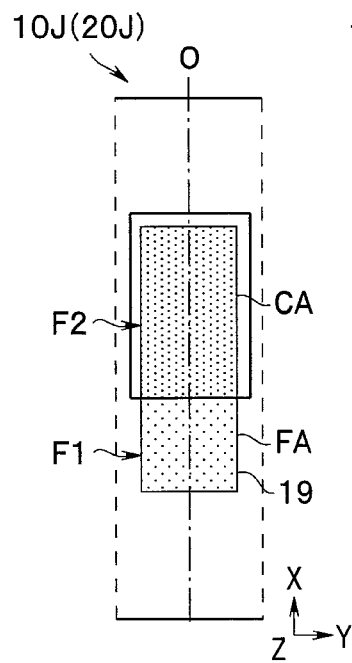
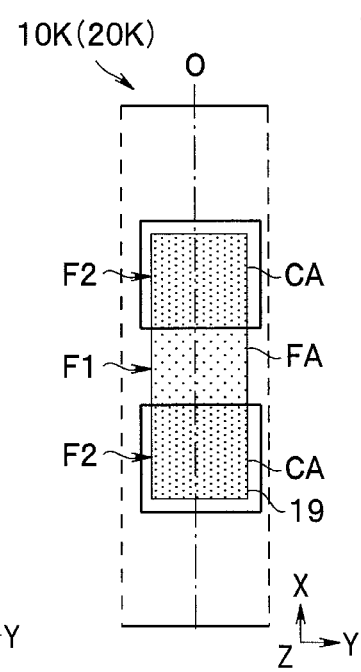
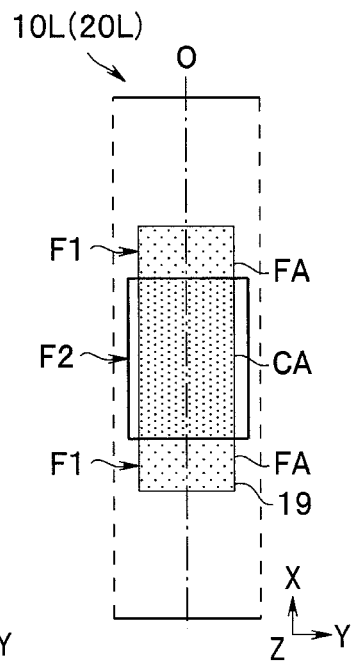

ULTRASONIC ELEMENT AND ENDOSCOPE

CROSS REFERENCE TO RELATED APPLICATION

This application is a continuation application of PCT/JP2019/033543 filed on Aug. 27, 2019, the entire contents of which are incorporated herein by this reference.

BACKGROUND OF THE INVENTION

1. Field of the Invention

The present invention relates to an ultrasonic element including a capacitive transducer, and to an endoscope including an ultrasonic probe that includes a plurality of ultrasonic elements each of which includes a capacitive transducer.

2. Description of the Related Art

An endoscope including an ultrasonic probe can clearly depict the digestive tract wall, the deep organs, or the like with a good image quality without being affected by gases or bones in the body. In an electronic scan ultrasonic probe, a plurality of ultrasonic elements are arranged in line, and each of the plurality of ultrasonic elements includes an ultrasonic transducer.

A ceramic piezoelectric material containing lead, for example, PZT (lead titanate zirconate) is often used for forming an ultrasonic transducer. On the other hand, there have been developments in a capacitive micro-machined ultrasonic transducer (hereinafter referred to as "cMUT") manufactured by using micromachine technology and made of a material containing no lead.

The cMUT emits or receives ultrasound with vibration of a membrane (diaphragm) including an upper electrode which faces a lower electrode with a cavity interposed between the upper electrode and the lower electrode.

With a harmonic imaging method that uses harmonic signals contained in reflected ultrasound, it is possible to obtain a clear image that cannot be obtained by a conventional B-mode method. The harmonic imaging method is classified into a tissue harmonic imaging and a contrast harmonic imaging. The tissue harmonic imaging uses a harmonic which is generated due to nonlinearity of the living tissue when ultrasound propagates through the living body. In the contrast harmonic imaging, contrast medium bubbles are injected into the body, and a harmonic is used which is generated when bubbles burst or resonate due to irradiation with ultrasound. The harmonic imaging requires an ultrasonic transducer having a wide band that can receive not only a fundamental frequency but also a harmonic, being an integral multiple of the fundamental frequency.

U. S. Patent Application Publication No. 2012/0123268 discloses a cMUT including a vibrating film (membrane) having a high aspect ratio. In such a cMUT, in a case where a distance from a center of the vibrating film to a periphery portion where the vibrating film is fixed is non-uniform, a high aspect ratio is selected to prevent sensitivity from being locally lowered.

International Publication No. 2005/087391 discloses a harmonic imaging method that uses a cMUT including an asymmetrical membrane where end portions have different widths.

U. S. Patent Application Publication No. 2009/0301200 discloses a cMUT where a beam structure is applied to a membrane to continuously vary a fractional bandwidth while a constant resonance frequency is maintained.

SUMMARY OF THE INVENTION

An ultrasonic element includes: a substrate; a first electrode provided above the substrate; a frame member having a cavity above the first electrode, a shape of the cavity in cross section parallel to the first electrode having a length in a first direction longer than a width in a second direction orthogonal to the first direction; a second electrode covering the cavity, and disposed to face the first electrode with the cavity interposed between the second electrode and the first electrode; and a protective layer covering the second electrode and having a convex region extending in the first direction, a width of the convex region in the second direction varying.

An endoscope according to another embodiment includes an ultrasonic element, wherein the ultrasonic element includes: a substrate; a first electrode provided above the substrate; a frame member having a cavity above the first electrode, a shape of the cavity in cross section parallel to the first electrode having a length in a first direction longer than a width in a second direction orthogonal to the first direction; a second electrode covering the cavity, and disposed to face the first electrode with the cavity interposed between the second electrode and the first electrode; and a protective layer covering the second electrode and having a convex region extending in the first direction, a width of the convex region in the second direction varying.

BRIEF DESCRIPTION OF THE DRAWINGS

FIG. 10A is a plan view of a cMUT of a modification 7 of the first embodiment;

FIG. 10B is a plan view of a cMUT of a modification 8 of the first embodiment;

FIG. 10C is a plan view of a cMUT of a modification 9 of the first embodiment;

FIG. 11A is a plan view of a cMUT of a modification 10 of the first embodiment;

FIG. 11B is a plan view of a cMUT of a modification 11 of the first embodiment;

FIG. 11C is a plan view of a cMUT of a modification 12 of the first embodiment;

DETAILED DESCRIPTION OF THE PREFERRED EMBODIMENTS

First Embodiment

Hereinafter, an ultrasonic element 20 (hereinafter also referred to as "element 20") of a first embodiment and an endoscope 2 including the ultrasonic elements 20 will be described with reference to drawings.

<Endoscope System>

Figure 1:
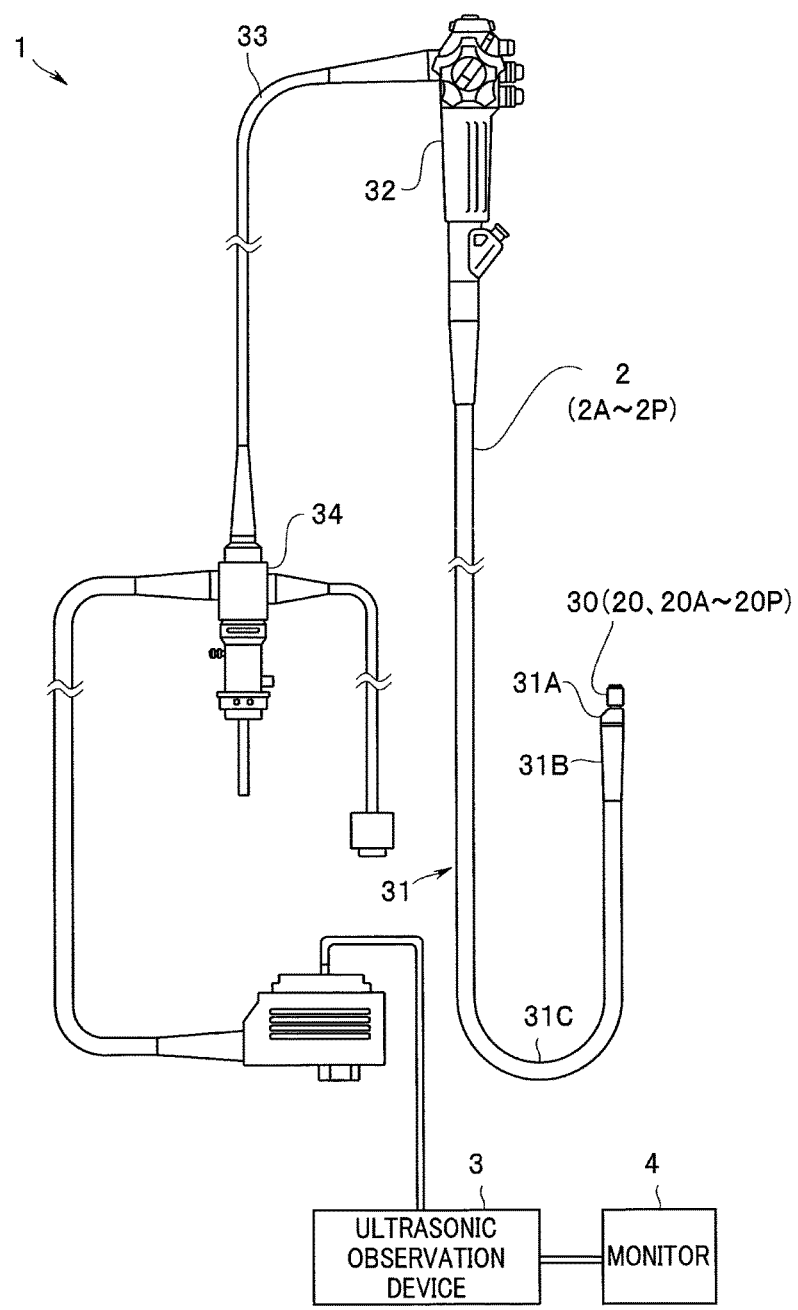
FIG. 1 is a schematic view of an endoscope system including an endoscope of an embodiment.

The endoscope 2 shown in FIG. 1 forms an endoscope system 1 together with an ultrasonic observation device 3 and a monitor 4. The endoscope 2 includes an elongated insertion portion 31, an operation portion 32, and an universal cord 33, the insertion portion 31 being to be inserted into the body, the operation portion 32 being provided at a proximal end of the insertion portion 31, the universal cord 33 extending from the operation portion 32.

A connector 34 is provided to the universal cord 33 and is connected with a light source device (not shown in the drawing), a camera control unit (not shown in the drawing), and the ultrasonic observation device 3. The monitor 4 is connected to the ultrasonic observation device 3 and the camera control unit.

The insertion portion 31 is formed by continuously providing a hard portion 31A, a bending portion 31B, and an elongated flexible tube portion 31C that has a small diameter and has flexibility. An ultrasonic probe 30, serving as an ultrasound transmitting and receiving unit, is provided to the hard portion 31A.

<Ultrasonic Probe>

Figure 2:
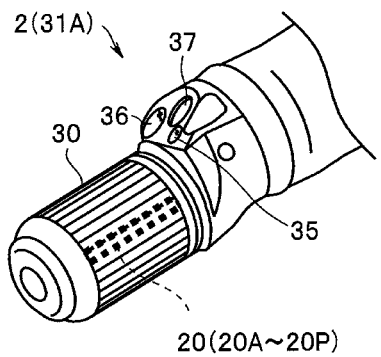
FIG. 2 is a perspective view of a distal end portion of the endoscope of the embodiment.

The ultrasonic probe 30 of the endoscope 2 shown in FIG. 2 is a radial ultrasonic probe where a plurality of elongated rectangular ultrasonic elements 20 are arranged in a curved manner into a cylindrical shape by coupling long sides of the ultrasonic elements 20 to each other. The hard portion 31A is provided with an illumination lens cover 35 forming an illumination optical system, an observation lens cover 36 of an observation optical system, a forceps port 37 also serving as a suction port, and an air/water feeding nozzle not shown in the drawing.

The ultrasonic probe 30 may be a convex ultrasonic probe where a plurality of elements 20 are arranged in a curved manner into a convex shape.

<Ultrasonic Element>

Figure 3:
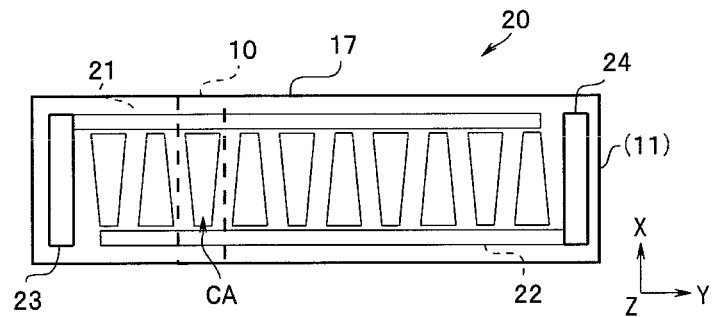
FIG. 3 is a plan view of an ultrasonic element of a first embodiment.
Figure 4:
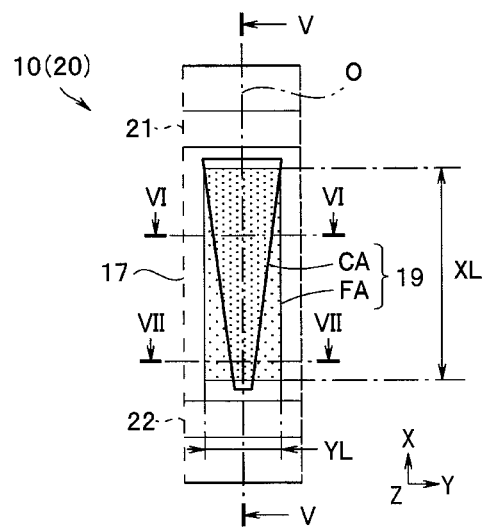
FIG. 4 is a plan view of a cMUT of the first embodiment.

In the element 20 shown in FIG. 3, a plurality of rectangular capacitive transducers (cMUTs) 10 are integrated with long sides of the respective cMUTs 10 being disposed adjacent to each other, and are arranged in line on one substrate 11. The following drawings are schematic views provided for the purpose of description, and thicknesses, sizes, ratios of dimensions and the like of respective constitutional elements may be different from thicknesses, sizes, ratios of dimensions and the like of respective constitutional elements of an actual cMUT. Further, in describing a stack structure of the element 20, a side where the substrate 11 is disposed is referred to as "lower", and a side disposed on a surface from which ultrasound is emitted is referred to as "upper".

Figure 5:
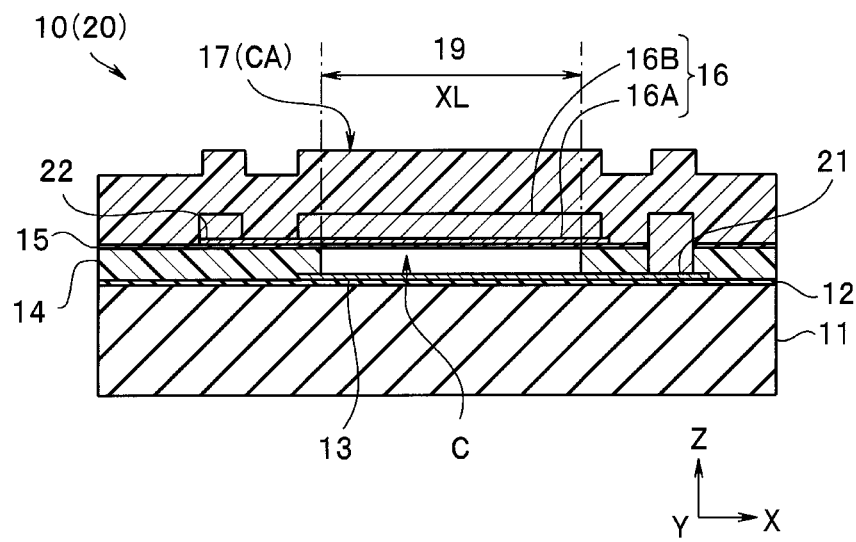
FIG. 5 is a cross-sectional view of the cMUT of the first embodiment taken along line V-V in FIG. 4.

An upper surface (a surface disposed on a side opposite to the substrate 11) of the element 20 is covered by a protective layer 17 except for a region where electrode terminals 23, 24 are provided. In other words, a first wiring 21 (a third conductive layer 21A) and a second wiring 22 (a third conductive layer 22A) are also covered by the protective layer 17 (see FIG. 5). The first wiring 21 (the third conductive layer 21A) connects first electrodes (lower electrodes) 13 of the plurality of cMUTs 10 with each other, and the second wiring 22 (the third conductive layer 22A) connects second electrodes (upper electrodes) 16 of the plurality of cMUTs 10 with each other.

A region of the protective layer 17 that covers a second conductive layer 16B of the second electrode 16 (see FIG. 5 to FIG. 8) forms a convex region CA. A thickness of the protective layer 17 in the convex region CA is substantially equal to a thickness of the protective layer 17 in a flat region FA, which is disposed around the convex region CA. However, the convex region CA covers the second conductive layer 16B, thus protruding from the flat region FA by an amount corresponding to a thickness of the second conductive layer 16B. A shape of the convex region CA in cross section parallel to a principal surface of the substrate 11 is a trapezoidal shape.

Regions of the protective layer 17 that cover the first wiring 21 (the third conductive layer 21A) and the second wiring 22 (the third conductive layer 22A) also have a convex shape.

In the element 20 shown in FIG. 3, the adjacent cMUTs 10 are arranged in a state where the convex region CA of one cMUT 10 is rotated by 180 degrees from the convex region CA of the adjacent cMUT 10. However, the adjacent cMUTs 10 may be arranged in a state where a direction of the convex regions CA of one cMUT 10 is equal to a direction of the convex regions CA of the other cMUT 10.

The element 20 may be formed of one cMUT.

<cMUT>

Next, a structure of the cMUT 10 of the element 20 will be described with reference to FIG. 4 to FIG. 8.

The cMUT 10 includes a first insulation layer 12, the first electrode (lower electrode) 13, a frame member 14, a second insulation layer 15, the second electrode (upper electrode) 16, and the protective layer 17 which are arranged on the substrate 11 in this order. The frame member 14 has a cavity C above the first electrode 13. The second electrode 16 is disposed to face the first electrode 13 with the cavity C of the frame member 14 interposed between the second electrode 16 and the first electrode 13. The protective layer 17 covers an upper surface of the cMUT 10 including the second electrode 16.

The second electrode 16 includes a first conductive layer 16A and the second conductive layer 16B. The first conductive layer 16A completely covers an upper side of the cavity C, and the second conductive layer 16B covers only a portion of the first conductive layer 16A. The thickness of the second conductive layer 16B is larger than a thickness of the first conductive layer 16A.

The first insulation layer 12 and the second insulation layer 15 are not essential constitutional elements of the cMUT 10. For example, in a case where the substrate 11 is made of an insulating material, the first insulation layer 12 is not necessary.

The second electrode 16 and the protective layer 17 disposed above the cavity C form a membrane (vibrating film) 19 which ultrasonically vibrates. With vibration of the membrane 19, the cMUT 10 emits ultrasound in a vertical direction (Z direction) with respect to the membrane 19. In the cMUT 10, the membrane 19 vibrates due to ultrasound which is incident from the vertical direction (Z direction).

A shape of the cavity C in cross section (XY plane) parallel to the first electrode 13, in other words, a shape of the cavity C in cross section (XY plane) perpendicular to a direction of vibration of the membrane 19 (Z direction) is a substantially rectangular shape where a length in a first direction (X axis direction) is longer than a length in a second direction (Y axis direction), which is orthogonal to the first direction. The first electrode 13 faces the second conductive layer 16B with the cavity C interposed between the first electrode 13 and the second conductive layer 16B. A cross section of a region of the first electrode 13 that faces the cavity C has the same size and the same shape as the cavity C. A cross section of a region of the second conductive layer 16B that faces the cavity C has the same size and the same shape as the cavity C.

For example, a length XL of the rectangular cavity C in the first direction (X axis direction: long axis direction) is 30 μm to 3000 μm, and a length (width) YL of the rectangular cavity C in the second direction (Y axis direction: short axis direction) is 5 μm to 500 μm. It is preferable that an aspect ratio (XL/YL), which is a ratio of the length XL to the width YL of the cavity C, be 6 or more and 20 or less. When the aspect ratio (XL/YL) of the cavity C falls within the above-mentioned range, the cMUT 10 can achieve a wide band and high efficiency.

In the cMUT 10 of the embodiment, an area where the first electrode 13 faces the second electrode 16 is equal to an area of the cavity C in cross section (XY plane parallel to the first electrode 13) perpendicular to the direction of vibration of the membrane 19 (Z direction). In other words, the first electrode 13 covers an entire lower side of the cavity C, and the second electrode 16 covers an entire upper side of the cavity C.

The area where the first electrode 13 faces the second electrode 16 with the cavity C interposed between the first electrode 13 and the second electrode 16 is equal to the area of the cavity C, thus being large. Accordingly, the cMUT 10 (the element 20) of the embodiment has high transmission and reception efficiency.

For example, the thickness of the first conductive layer 16A is 0.1 μm, and the thickness of the second conductive layer 16B is 2 μm. It is preferable that the thickness of the first conductive layer 16A be 0.05 μm or more and 0.5 μm or less, and the thickness of the second conductive layer 16B be 1 μm or more and 10 μm or less.

In other words, it is sufficient that a voltage can be applied between the first conductive layer 16A and the first electrode 13, which is disposed to face the first conductive layer 16A. Therefore, the first conductive layer 16A has a small thickness. In contrast, the second conductive layer 16B applies a predetermined weight distribution to the membrane 19, thus having a large thickness.

Figure 6:
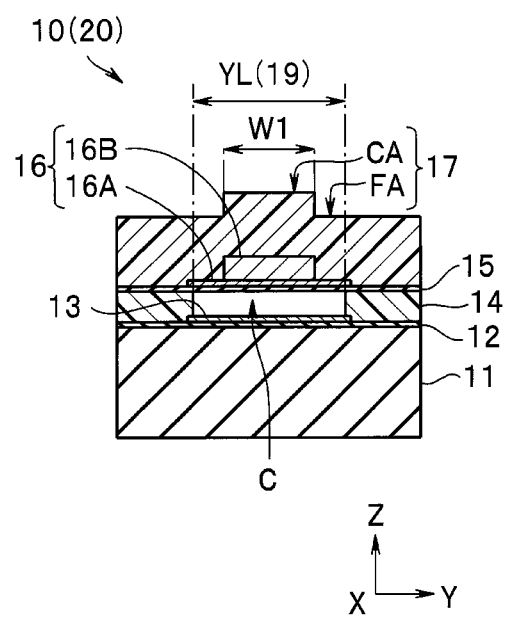
FIG. 6 is a cross-sectional view of the cMUT of the first embodiment taken along line VI-VI in FIG. 4.

The second conductive layer 16B extends in the first direction (X axis direction). A width W of the second conductive layer 16B in the second direction (Y axis direction) is not constant, and varies linearly. A shape of the second conductive layer 16B in cross section parallel to the first electrode 13 is a trapezoidal shape that is axially symmetric about a center line O with respect to a width (length) YL of the membrane 19 in the second direction. A width W1 in the cross section shown in FIG. 6 is larger than a width W2 in a cross section shown in FIG. 7.

A resonance frequency of the membrane 19 decreases or increases in proportion to a weight and hardness of the membrane 19. Therefore, a region with a large width W1 of the second conductive layer 16B has a higher resonance frequency than a region with a small width of the second conductive layer 16B. The resonance frequency of the membrane 19 varies in the first direction and hence, the membrane 19 has a wide band.

The center line O of the membrane 19 has the largest amplitude when the membrane 19 vibrates. In other words, the membrane 19 is deformed the most along the center line O. The membrane 19 of the ultrasonic element 20 is reinforced along the center line O by the second conductive layer 16B having a large thickness and hence, the membrane 19 has excellent durability.

The region of the protective layer 17 that covers the second conductive layer 16B forms the convex region CA due to the thickness of the second conductive layer 16B. In other words, the shape of the convex region CA is substantially equal to the shape of the second conductive layer 16B. The convex region CA extends in the first direction (X axis direction). The width W of the convex region CA in the second direction (Y axis direction) varies and hence, the convex region CA has a trapezoidal shape which is left-right symmetric about the center line O with respect to the width (length) YL of the membrane 19 in the second direction. The protective layer 17 forms the membrane 19, and a region of the protective layer 17 that is disposed around the convex region CA and that does not cover the second conductive layer 16B is referred to as the flat region FA.

The third conductive layers 21A, 22A made of the same material as and having the same thickness as the second conductive layer 16B are also respectively provided to the first wiring 21 and the second wiring 22.

It is preferable that the first wiring 21 and the second wiring 22 have a large thickness to reduce electric resistance. As will be described later, in a step of providing the second conductive layer 16B on the first conductive layer 16A, the third conductive layer 22A is provided on the second wiring 22 simultaneously in the element 20, for example. The first wiring 21 and the second wiring 22 have low resistance due to the third conductive layers 21A, 22A and hence, the element 20 can transmit and receive ultrasound having a higher frequency with a shorter delay time compared with an element having no third conductive layers 21A, 22A.

<Manufacturing Method>

Next, a method for manufacturing the element 20 including the cMUT 10 will be described.

The substrate 11 is made of silicon, for example. A surface of the substrate 11 is thermally oxidized to form a silicon oxide layer, which is the first insulation layer 12. The first insulation layer 12 may be a layer provided to the substrate 11, such as a resin layer or an inorganic material layer formed by a CVD method (chemical vapor deposition method) or the like by using SiN or the like.

A conductive layer made of metal, such as copper, aluminum, or gold, or doped silicon, is provided on the first insulation layer 12 of the substrate 11, that is, provided above the substrate 11. A mask pattern is provided by photolithography and, thereafter, the conductive layer is partially removed by using an etching method to form a patterned first electrode 13. The first electrode 13 extends to the first wiring 21 via a wiring which is caused to extend from an edge portion of the first electrode 13.

In the following description, the description of patterning performed by a photolithography method will be omitted.

A sacrificial layer pattern (not shown in the drawing) having a shape of the cavity C is provided in a state of covering the first electrode 13. Then, the second insulation layer 15 is provided in a state of covering the sacrificial layer pattern by a method and a material substantially equal to a method and a material used for forming the first insulation layer 12, for example.

A frame member layer 14 made of an insulating material, such as SiN, is provided in a state of covering the second insulation layer 15, and the second insulation layer 15 is provided in a state of covering the frame member layer 14. The second insulation layer 15 is made of SiN, for example.

An opening portion (not shown in the drawing) is formed in each of the frame member layer 14 and the second insulation layer 15 at a predetermined position. An etchant is caused to flow into the opening portions to remove the sacrificial layer pattern.

When the sacrificial layer pattern is removed, the cavity C is formed. For example, in a case where phospho silicate glass is used for forming the sacrificial layer pattern and SiN is used for forming the first insulation layer 12 and the second insulation layer 15, hydrofluoric acid solution (buffered HF solution) is used as an etchant.

In a case where the first electrode 13 is dissolved by an etchant, a third insulation layer, which covers the first electrode 13, is provided before the sacrificial layer pattern is provided. In contrast, in a case where the first electrode 13 and the second electrode 16 are not dissolved by an etchant, the second insulation layer 15 is not necessary. The second insulation layer 15 and the third insulation layer are formed by the same method and the same material.

The cavity C may be formed by a so-called bond-forming method. In the bond-forming method, the frame member layer 14 having a space, which forms the cavity C, is provided and, thereafter, the second electrode 16 is bonded to the frame member layer 14. Particularly, in a case where the cavity C has high aspect, the sacrificial layer pattern may not be easily etched and hence, it is preferable to use a bond-forming method.

The shape of the cavity C, that is, the membrane 19 in cross section (XY plane) parallel to the first electrode 13 may be a substantially rectangular shape where corner portions of a rectangular shape are chamfered, a trapezoidal shape, an elliptical shape, or other shapes.

Next, by using a method substantially equal to the method for forming the first electrode 13, the first conductive layer 16A of the second electrode 16 is provided in a state of covering the second insulation layer 15. The first conductive layer 16A completely covers an upper surface of the cavity C. Further, the first conductive layer 16A is caused to extend to the second wiring 22 via a wiring. The first conductive layer 16A, the wiring and the second wiring 22 are simultaneously formed and patterned, thus forming an integral conductive layer. The first conductive layer 16A or the like may include a layer made of chromium, titanium, or the like as a base layer.

The second conductive layer 16B is provided to a portion of the first conductive layer 16A, which forms the membrane 19. From a viewpoint of productivity and adhesion strength, it is preferable that the first conductive layer 16A and the second conductive layer 16B be made of the same material. For example, the first conductive layer 16A is a copper layer provided by a sputtering method, and the second conductive layer 16B is a copper plating layer.

The first conductive layer 16A may be formed in such a manner that a conductive film having the thickness of the second conductive layer 16B is provided, and a region of the conductive film other than a region forming the second conductive layer 16B is then thinned by etching, argon ion milling, or the like.

In the method for manufacturing the element 20, in a step of providing the second conductive layer 16B, the third conductive layers 21A, 22A are simultaneously provided on the first wiring 21 and the second wiring 22 respectively. More specifically, the third conductive layers 21A, 22A and the second conductive layer 16B are formed and patterned by the same method, made of the same material, and have the same thickness.

Conversely, in the method for manufacturing the element 20, to reduce wiring resistance, the second conductive layer 16B is provided simultaneously in a step of providing the third conductive layers 21A, 22A.

Only either one of the first electrode 13 or the first conductive layer 16A may be a common conductive layer for the plurality of cMUTs 10, the common conductive layer being provided over the plurality of cMUTs 10. For example, the first conductive layer 16A shown in FIG. 8 may be caused to extend in the second direction (Y axis direction) of the cMUT 10. The common conductive layer can be easily patterned and hence, an element including the common conductive layer can be easily manufactured. When each of both the first electrode 13 and the first conductive layer 16A is formed of a common conductive layer, parasitic capacitance increases. Therefore, such a configuration is not preferable.

The protective layer 17 is provided in a state of covering the second electrode 16. The protective layer 17 may be provided by a method and a material substantially equal to the method and the material used for forming the second insulation layer 15. The protective layer 17 may have a two-layered structure where an outer skin layer made of polyparaxylylene or the like and having biocompatibility is provided on a thin insulation layer made of SiN or the like.

A region of the protective layer 17 that covers the second conductive layer 16B forms the convex region CA which protrudes from the flat region FA covering only the first conductive layer 16A.

The cavity C may be formed in such a manner that the second electrode 16 or the protective layer 17 is provided and, thereafter, the sacrificial layer is etched.

<Driving Method>

The cMUT 10 has the cavity C (the membrane 19) having a substantially rectangular shape, and a resonance frequency FR of the cavity C (the membrane 19) continuously varies in the first direction (X axis direction), which is a longitudinal direction. More specifically, a region with a large width W of the second conductive layer 16B is harder than a region with a small width W of the second conductive layer 16B, thus having a higher resonance frequency FR.

Figure 7:
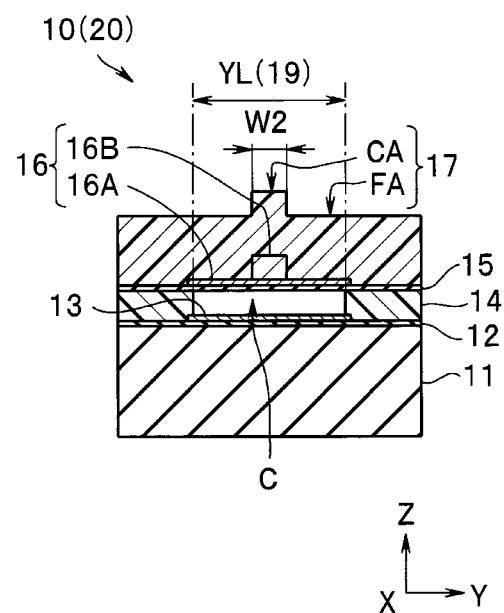
FIG. 7 is a cross-sectional view of the cMUT of the first embodiment taken along line VII-VII in FIG. 4.
Figure 8:
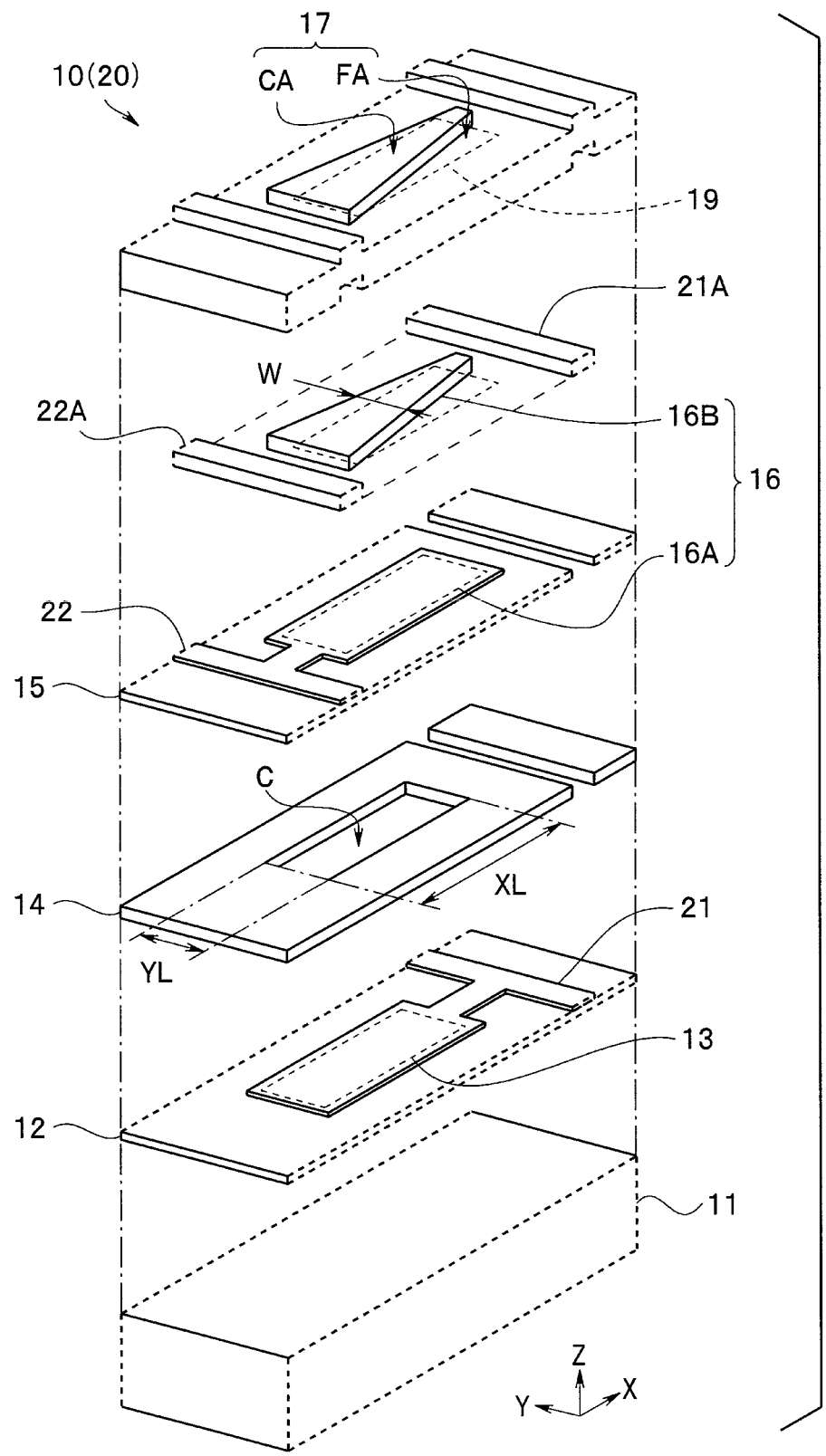
FIG. 8 is an exploded view of the cMUT of the first embodiment.

For example, a resonance frequency FR1 of a region with the width W2 shown in FIG. 7 is 10 MHz, and a resonance frequency FR2 of a region with the width W1, which is larger than the width W2, shown in FIG. 6 is 20 MHz.

When a drive signal having a fundamental frequency FR1 (10 MHz) is applied to the electrode terminals 23, 24 of the element 20, the cMUT 10 emits ultrasound having the fundamental frequency FR1 (10 MHz) mainly to the region with the width W2. Reflected ultrasound having a second harmonic FR2 (20 MHz) from an object vibrates mainly about the region with the width W1 in the cMUT 10.

The resonance frequency FR of the membrane 19 continuously varies in the first direction (X axis direction) and hence, the element 20 has a wide band. Further, the electrode that faces the membrane 19 has a large area and hence, the element 20 can achieve high efficiency.

To prevent harmonic ultrasound from being emitted, it is preferable that a drive signal applied to the element 20 have a sine wave rather than a rectangular wave. To obtain a signal having the harmonic FR2 that is not affected by reflected waves having the fundamental frequency FR1, it is preferable that drive signals having a fundamental frequency with an inverted phase be continuously applied, and signals of reflected ultrasound of the drive signals be processed. The reason is as follows. Reflected waves of ultrasound having a fundamental frequency with an inverted phase disappear with superimposition processing. However, harmonic reflected waves of ultrasound having a fundamental frequency with an inverted phase do not disappear even with superimposition processing.

The element 20 can achieve high efficiency and a wide band, so that the endoscope including the ultrasonic probe 30 which includes the element 20 can achieve high efficiency and a wide band. A resonance frequency of the element 20 has a wide band ranging from the fundamental frequency FR1 to the harmonic FR2, being an integral multiple of the fundamental frequency FRE Therefore, the element 20 can be suitably used particularly for a harmonic imaging methods.

Modifications of First Embodiment

Elements 20A to 20L of modifications 1 to 12 of the first embodiment will be described. Each of the elements 20A to 20L is similar to and has substantially the same advantageous effects as the element 20 and hence, corresponding constitutional elements are given the same reference symbols, and the description of such constitutional elements will be omitted.

In any one of cMUTs 10A to 10L of the elements 20A to 20L, an upper surface of the membrane 19 (the protective layer 17) has the convex region CA which protrudes from the flat region FA covering the first conductive layer 16A. The convex region CA is formed by covering the second conductive layer 16B.
<Modifications 1, 2>

Figure 9A:
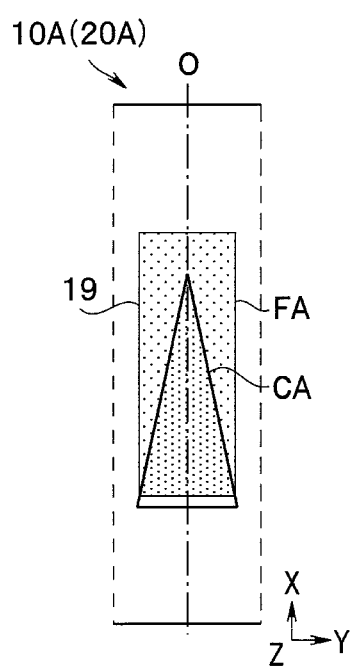
FIG. 9A is a plan view of a cMUT of a modification 1 of the first embodiment.

In the cMUT 10A of the element 20A of the modification 1 shown in FIG. 9A, the membrane 19 (the protective layer 17) has the flat region FA in the first direction (X axis direction), the flat region FA having no convex region CA. In other words, the cMUT 10A has the flat region FA where the width W of the convex region CA is zero.

Figure 9B:
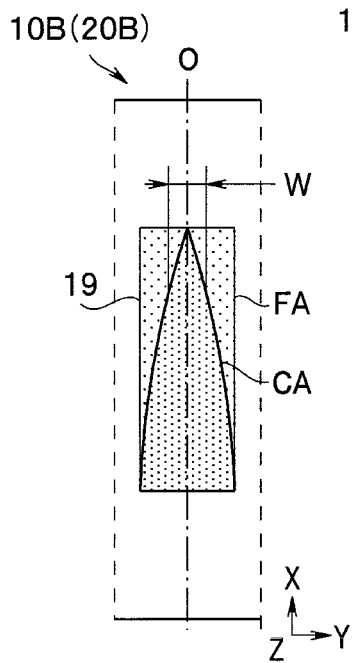
FIG. 9B is a plan view of a cMUT of a modification 2 of the first embodiment.

In the membrane 19 (the protective layer 17) of the cMUT 10B of the element 20B of the modification 2 shown in FIG. 9B, the width W of the convex region CA varies in a curved manner in the first direction (X axis direction).

In other words, variations in width W of the convex region CA are not limited to a linear variations, and may include curved variations.
<Modifications 3 to 6>

Figure 9C:
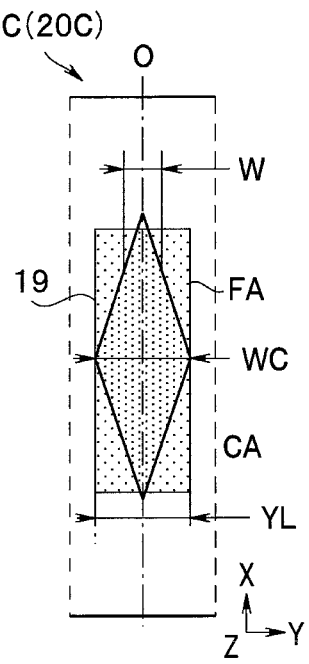
FIG. 9C is a plan view of a cMUT of a modification 3 of the first embodiment.

In the cMUT 10C of the element 20C of the modification 3 shown in FIG. 9C, the convex region CA has a substantially rhombus shape. The width W of the convex region CA linearly varies in the first direction (X axis direction), and a width WC of the convex region CA at a center portion is the largest in the convex region CA. The width WC is equal to the width YL of the membrane 19.

Figure 9D:
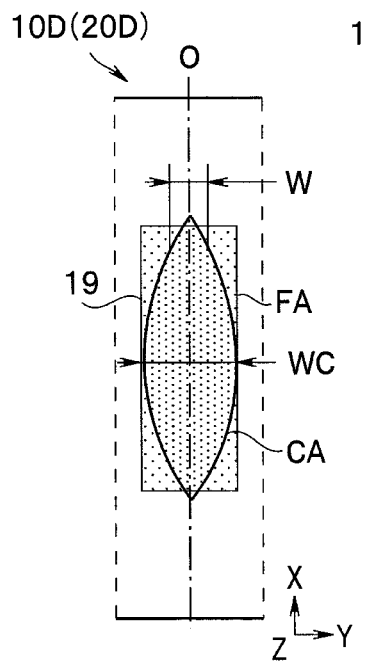
FIG. 9D is a plan view of a cMUT of a modification 4 of the first embodiment.

In the cMUT 10D of the element 20D of the modification 4 shown in FIG. 9D, the convex region CA has a substantially football shape. The width W of the convex region CA varies in a curved manner, and a width WC of the convex region CA at a substantially center portion is the largest in the convex region CA.

Figure 9E:
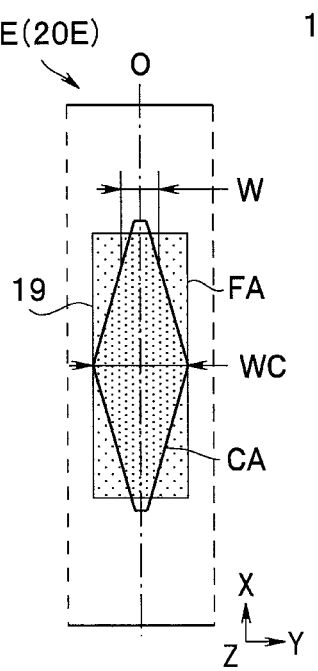
FIG. 9E is a plan view of a cMUT of a modification 5 of the first embodiment.

In the cMUT 10E of the element 20E of the modification 5 shown in FIG. 9E, the convex region CA has a substantially barrel shape. The width W of the convex region CA varies linearly, and the width WC of the convex region CA at a substantially center portion in the first direction (X axis direction) of the membrane 19 is the largest in the convex region CA.

Figure 9F:
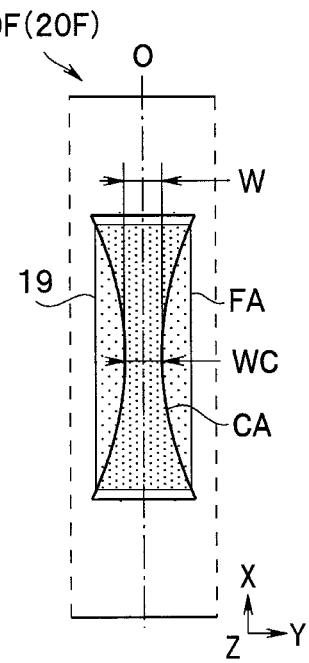
FIG. 9F is a plan view of a cMUT of a modification 6 of the first embodiment.

In the cMUT 10F of the element 20F of the modification 6 shown in FIG. 9F, the convex region CA has a hourglass drum shape having a narrowed substantially center portion. The width W of the convex region CA varies in a curved manner, and the width WC of the convex region CA at a substantially center portion in the first direction (X axis direction) of the membrane 19 is the smallest width of the convex region CA.

In other words, the width W of the convex region CA of the cMUT 10 of the element may vary linearly or may vary in a curved manner. Further, variation in the width W of the convex region CA is not necessarily a monotone variation. The width W of the convex region CA may vary in the first direction (X axis direction) in such a manner that the width W of the convex region CA takes the maximum value or the minimum value and then reduces or increases. In other words, the width W of the convex region CA at the substantially center portion in the first direction of the membrane 19 may be the largest or the smallest in the convex region CA.

Modifications 7 to 12

In the cMUT where the width W of the convex region CA continuously varies, a narrow region in the first direction (X axis direction) has a predetermined resonance frequency. In contrast, in the cMUTs 10G to 10L of the elements 20G to 20L of the modifications 7 to 12, the width W of the convex region CA varies stepwise. Therefore, a region having a target resonance frequency has a large area. In other words, the elements 20G to 20L of the modifications 7 to 12 have high transmission sensitivity and reception sensitivity at a desired frequency, thus having high efficiency.

Modifications 7 to 9

In the cMUTs 10G to 10I of the elements 20G to 20I of the modifications 7 to 9 shown in FIGS. 10A to 10C, the width W of the convex region CA varies stepwise in two stages, and the flat region FA is provided where the convex region CA is not provided in the second direction (Y axis direction). A region where the width W of the convex region CA is the largest in the convex region CA is formed only of the convex region CA.

A region F1 has no convex region CA and the entire region F1 is formed of the flat region FA. A resonance frequency of the region F1 is set to a fundamental frequency f1. A region F2 is partially formed of the convex region CA. A resonance frequency of the region F2 is a harmonic two times as large as the fundamental frequency f1. An entire region F3 is formed of the convex region CA. A resonance frequency of the region F3 is a third harmonic three times as large as the fundamental frequency f1.

In other words, the membrane 19 of each of the elements 20G to 20I is formed of three regions having different resonance frequencies.

<Modifications 10 to 12>

In the cMUTs 10J to 10L of the elements 20J to 20L of the modifications 10 to 12 shown in FIGS. 11A to 11C, the membrane 19 has a region formed of the convex region CA and the flat region FA in the first direction, the flat region FA having no convex region CA.

A region F1 has no convex region CA and is formed of the flat region FA. The resonance frequency of the region F1 is set to the fundamental frequency f1. An entire region F2 is formed of the convex region CA. The resonance frequency of the region F2 is a second harmonic twice as large as the fundamental frequency f1.

In other words, the membrane 19 of each of the elements 20J to 20L is formed of two regions F1, F2 having different resonance frequencies.

It is preferable that a region where the resonance frequency is a harmonic frequency, that is, the region F2, F3 where the entire region is formed of the convex region CA have an area larger than an area of a region where the resonance frequency is a fundamental frequency, that is, the region F1 having no convex region CA and formed of the flat region FA. The reason for this is to receive, with high sensitivity, harmonics having low intensity and contained in reflected waves of ultrasound having the fundamental frequency.

Further, intensity of the third harmonic is lower than intensity of the second harmonic. Therefore, it is preferable that an area of the region F3 that receives the third harmonic be larger than an area of the region F2 that receives the second harmonic.

The element may include two or more kinds of cMUTs selected from the cMUT 10 to the cMUT 10L of the first embodiment and the modifications 1 to 12 of the first embodiment.

Second Embodiment

An element 20M of a second embodiment will be described. The element 20M is similar to and has substantially the same advantageous effects as the element 20 and hence, corresponding constitutional elements are given the same reference symbols, and the description of such constitutional elements will be omitted.

Figure 12:
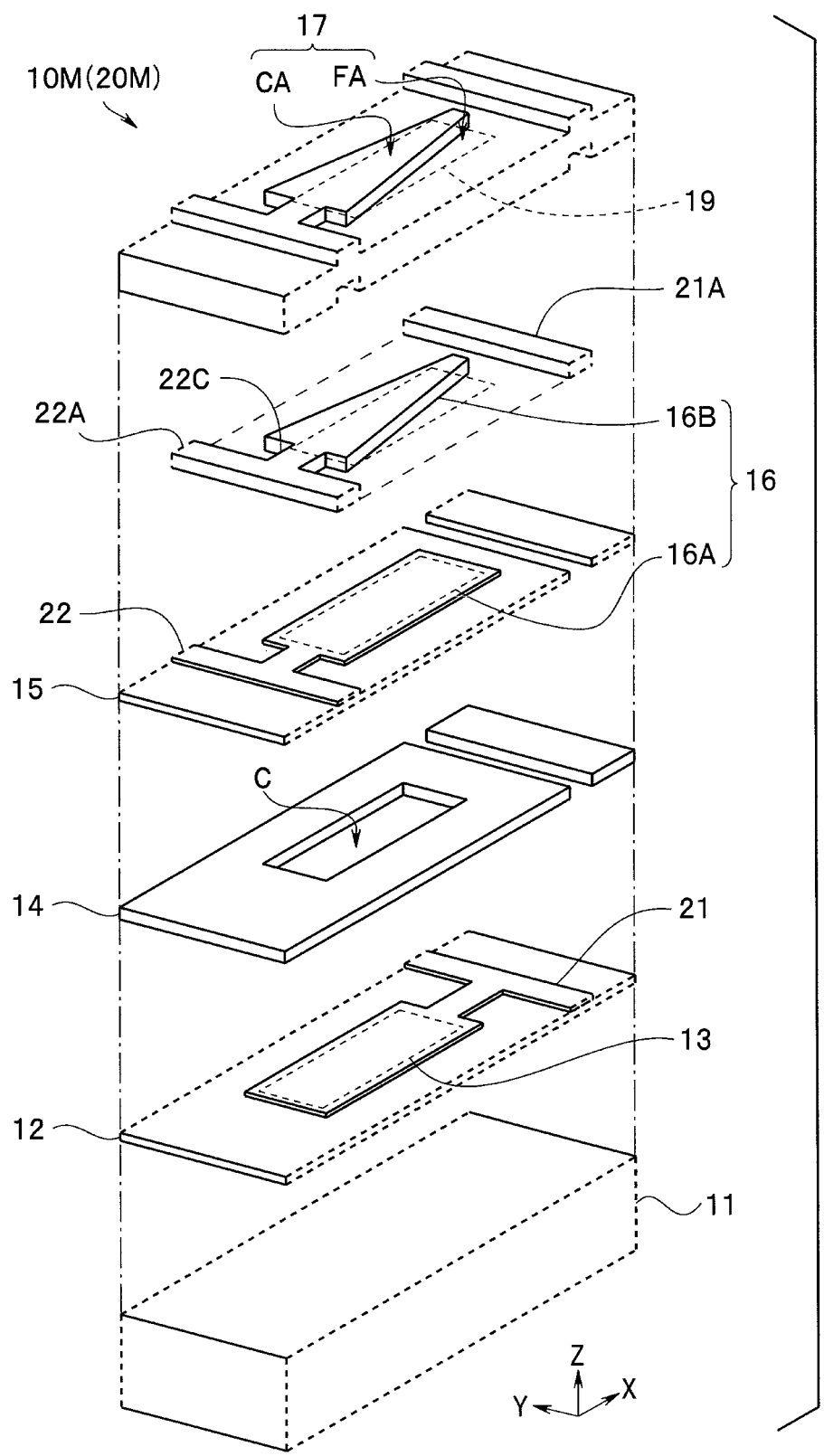
FIG. 12 is an exploded view of a cMUT of a second embodiment.

In a cMUT 10M of the element 20M shown in FIG. 12, a wiring between the second wiring 22 and the first conductive layer 16A is also covered by a third conductive layer 22C having the same thickness as and made of the same material as the second conductive layer. Therefore, the convex region CA of the protective layer 17 is connected with a convex region that covers the second wiring 22.

In the element 20M, a path from the second wiring 22 to the second electrode 16 has small electric resistance. Therefore, the element 20M can achieve high-efficiency transmission and reception.

When any of the elements 20A to 20L having the configurations shown in the modifications 1 to 12 of the first embodiment is provided and the second conductive layer covering the second wiring is caused to extend to the wiring between the second wiring 22 and the first conductive layer 16A, needless to say, it is possible to obtain an advantageous effect substantially equal to the advantageous effect which can be obtained by the element 20M in addition to the advantageous effect which can be obtained by the elements 20A to 20L.

Figure 13:
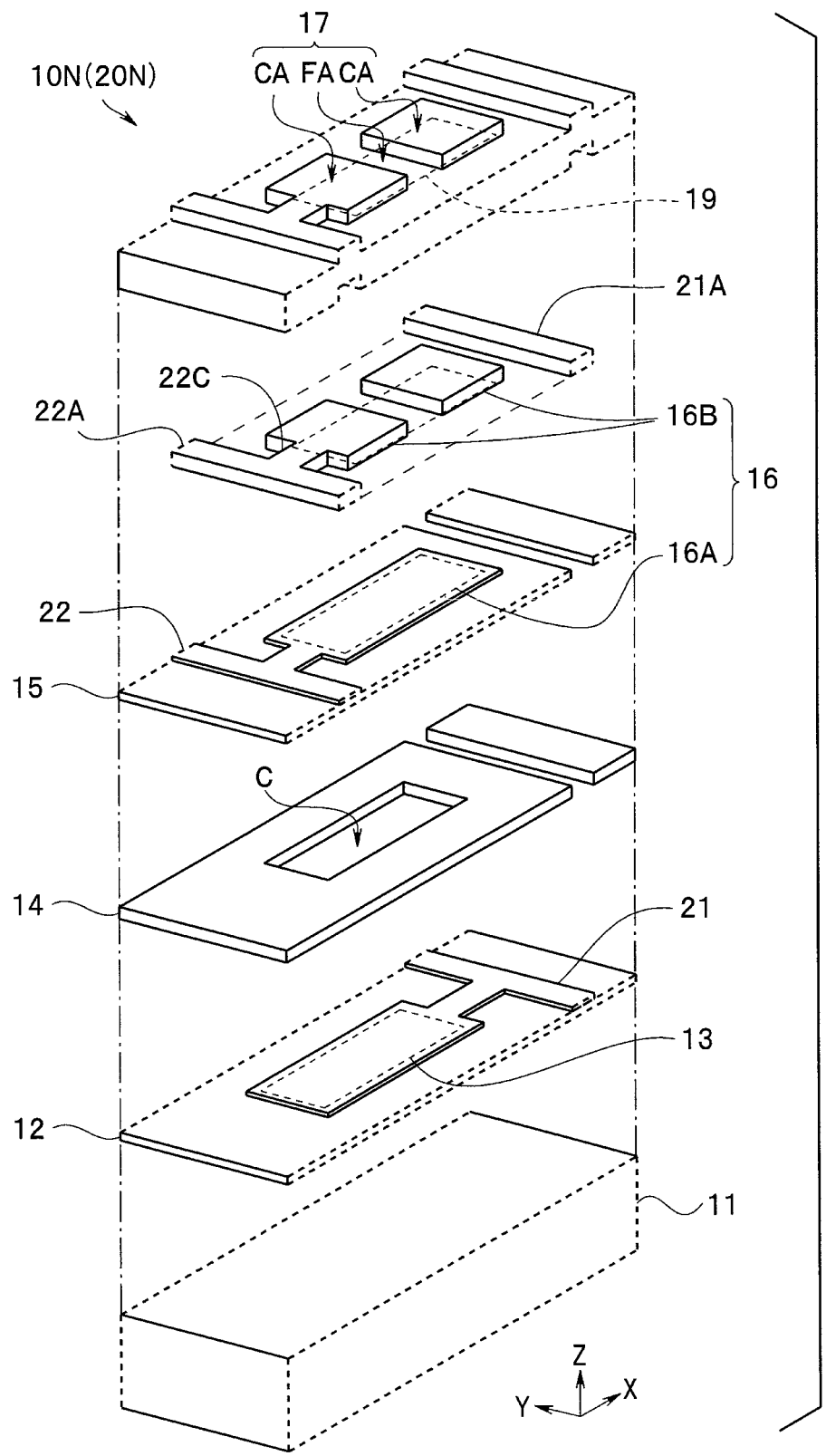
FIG. 13 is an exploded view of a cMUT of a modification of the second embodiment.

For example, in an element 20N of a modification of the second embodiment shown in FIG. 13, a cMUT 10N is equal to the cMUT 10K shown in FIG. 11B with respect to a point that the cMUT 10N is formed of two regions having different resonance frequencies. The element 20N has advantageous effects which can be obtained by the element 20M and the element 20K.

Third Embodiment

An element 20O of a third embodiment will be described. The element 20O is similar to and has substantially the same advantageous effects as the element 20 and hence, corresponding constitutional elements are given the same reference symbols, and the description of such constitutional elements will be omitted.

Figure 14:
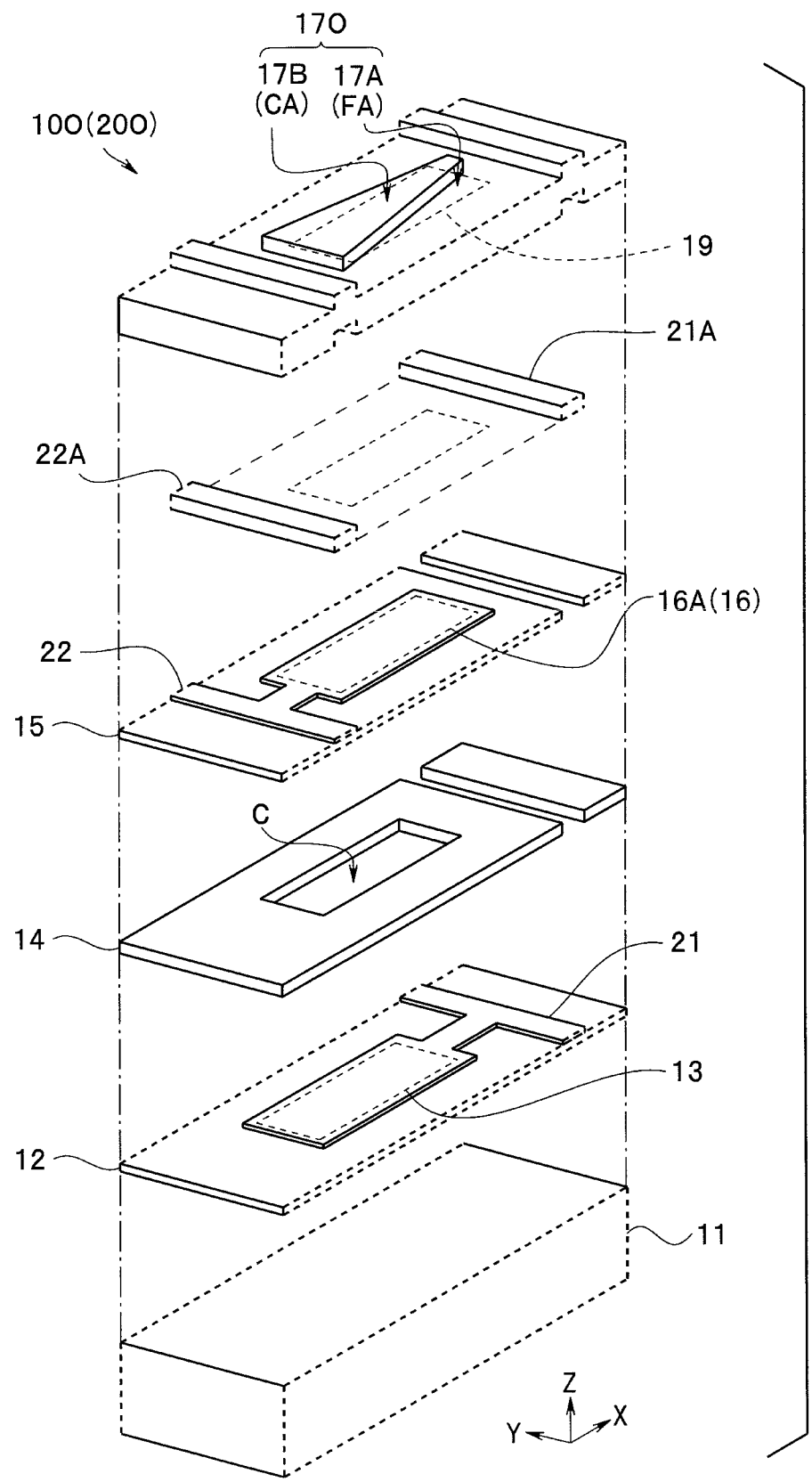
FIG. 14 is an exploded view of a cMUT of a third embodiment.

In a protective layer 17O shown in FIG. 14, a region where the protective layer 17O has a large thickness forms the convex region CA. In the protective layer 17O, a second protective layer 17B is stacked in a region of a first protective layer 17A that forms the convex region CA.

The frequency band can be widened by merely changing the thickness of the protective layer and hence, the element 20O can be easily manufactured.

When any of the elements 20A to 20L having the configurations shown in the modifications 1 to 12 of the first embodiment is provided and the convex region CA, where the protective layer 17O has a large thickness, is provided, needless to say, it is possible to obtain an advantageous effect substantially equal to the advantageous effect which can be obtained by the element 20O in addition to the advantageous effect which can be obtained by the element 20A to 20L.

Figure 15:
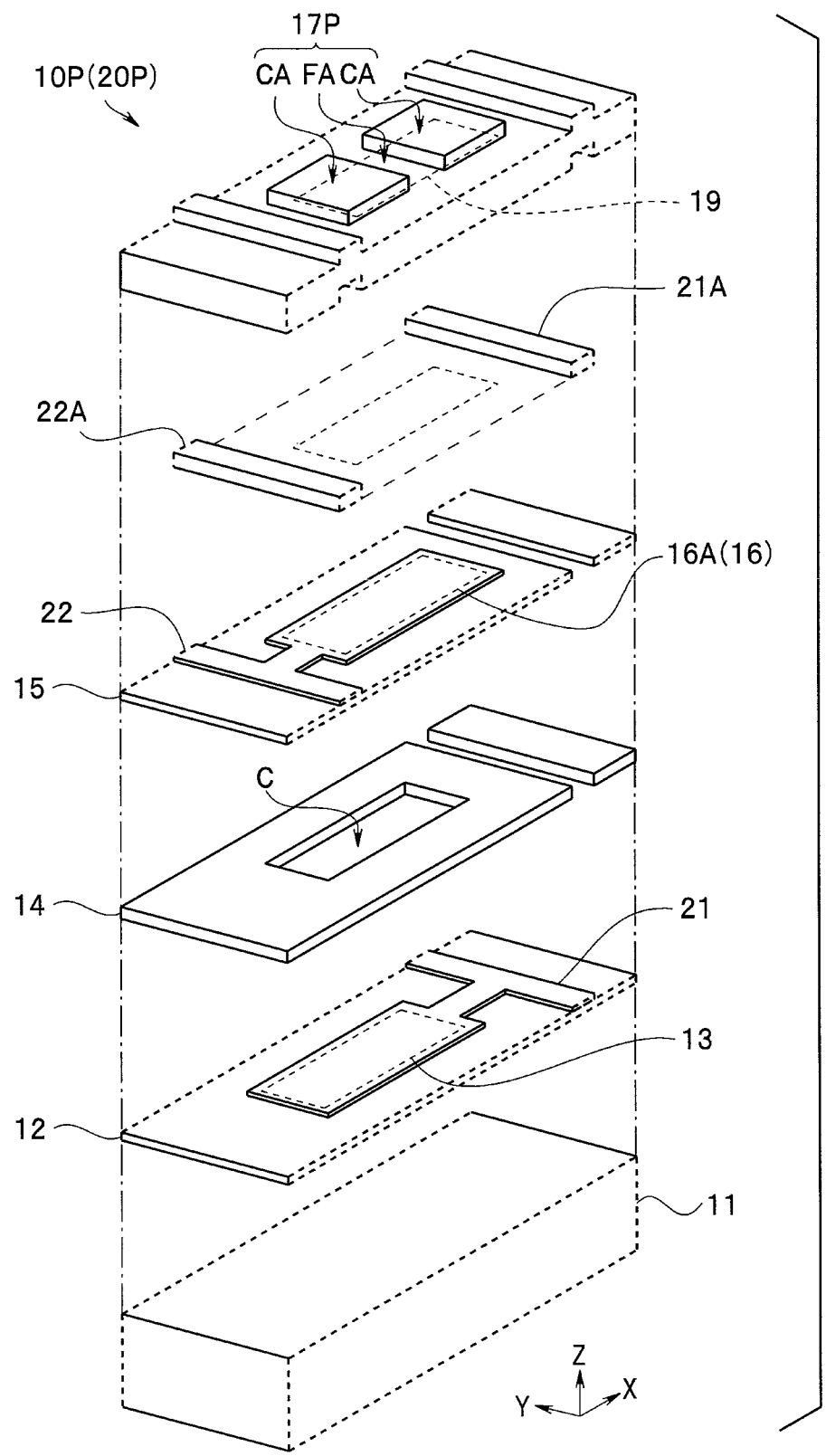
FIG. 15 is an exploded view of a cMUT of a modification of the third embodiment.

For example, in an element 20P of a modification of the third embodiment shown in FIG. 15, a cMUT 10P is equal to the cMUT 10K shown in FIG. 11B with respect to a point that the cMUT is formed of two regions having different resonance frequencies. The element 20P has advantageous effects which can be obtained by the element 20O and the element 20K.

Needless to say, an endoscope 2A to 2O including the element 20A to 20O has the advantageous effect which can be obtained by the endoscope 2 and the advantageous effect which can be obtained by the element 20A to 20O.

The present invention is not limited to the embodiment explained above. Various changes, alterations, and the like are possible within a range not changing the gist of the invention.

What is claimed is:

1. An ultrasonic element comprising:
   a substrate;
   a first electrode provided above the substrate;
   a frame member having a cavity above the first electrode,
      a shape of the cavity in cross section parallel to the first electrode having a length in a first direction longer than a width in a second direction orthogonal to the first direction;
   a second electrode covering the cavity, and disposed to face the first electrode with the cavity interposed between the second electrode and the first electrode; and a protective layer covering the second electrode and having a convex region extending in the first direction, a width of the convex region in the second direction varying;

wherein the second electrode includes a first conductive layer and a second conductive layer, the first conductive layer covering the cavity, the second conductive layer covering a portion of the first conductive layer, the second conductive layer has a thickness larger than a thickness of the first conductive layer and extends in the first direction, a width of the second conductive layer in the second direction varying, and the convex region is a region that covers the second conductive layer.

2. The ultrasonic element according to claim 1, wherein a shape of the second conductive layer in cross section parallel to the first electrode is axially symmetric about an axis of symmetry, the axis of symmetry being a center line of the width of the cavity in the second direction.

3. The ultrasonic element according to claim 1, wherein a material used for forming the first conductive layer is same as a material used for forming the second conductive layer.

4. The ultrasonic element according to claim 1, wherein a plurality of capacitive transducers are arranged in line on the substrate, the ultrasonic element comprises a second wiring connected with the second electrode of each of the plurality of capacitive transducers, the second wiring being made of a same material as and having a same thickness as the first conductive layer, and a third conductive layer covers the second wiring, the third conductive layer being made of a same material as and having a same thickness as the second conductive layer.

5. The ultrasonic element according to claim 4, wherein the third conductive layer, which covers the second wiring, also covers a wiring between the second wiring and the first conductive layer.

6. The ultrasonic element according to claim 4, wherein only either one of the first electrode or the second conductive layer forms a common conductive layer for the plurality of capacitive transducers, the common conductive layer being provided over the plurality of capacitive transducers.

7. The ultrasonic element according to claim 1, wherein the width of the convex region in the second direction varies linearly.

8. The ultrasonic element according to claim 1, wherein a width of the convex region at a center portion in the first direction is largest or smallest in the convex region.

9. The ultrasonic element according to claim 1, wherein the protective layer has a flat region in the first direction, the flat region having no convex region.

10. The ultrasonic element according to claim 1, wherein the width of the convex region in the second direction varies stepwise.

11. The ultrasonic element according to claim 1, wherein a membrane includes the second electrode and the protective layer, and is formed of two regions having different resonance frequencies.

12. The ultrasonic element according to claim 1, wherein a membrane includes the second electrode and the protective layer, and is formed of three regions having different resonance frequencies.

13. An endoscope comprising:
an ultrasonic element, wherein the ultrasonic element comprises:
a substrate;
a first electrode provided above the substrate;
a frame member having a cavity above the first electrode, a shape of the cavity in cross section parallel to the first electrode having a length in a first direction longer than a width in a second direction orthogonal to the first direction;
a second electrode covering the cavity, and disposed to face the first electrode with the cavity interposed between the second electrode and the first electrode; and
a protective layer covering the second electrode and having a convex region extending in the first direction, a width of the convex region in the second direction varying;
wherein the second electrode includes a first conductive layer and a second conductive layer, the first conductive layer covering the cavity, the second conductive layer covering a portion of the first conductive layer,
the second conductive layer has a thickness larger than a thickness of the first conductive layer and extends in the first direction, a width of the second conductive layer in the second direction varying, and
the convex region is a region that covers the second conductive layer.

14. An ultrasonic element comprising:
a substrate;
a first electrode provided above the substrate;
a frame member having a cavity above the first electrode, a shape of the cavity in cross section parallel to the first electrode having a length in a first direction longer than a width in a second direction orthogonal to the first direction;
a second electrode covering the cavity, and disposed to face the first electrode with the cavity interposed between the second electrode and the first electrode; and
a protective layer covering the second electrode and having a convex region extending in the first direction, a width of the convex region in the second direction varies one of linearly or stepwise.

* * * * *